United States Patent [19]

Yoshida et al.

[11] Patent Number: 4,814,532

[45] Date of Patent: Mar. 21, 1989

[54] PROCESS FOR PRODUCING ALKYLCYCLOPENTADIENE DERIVATIVES

[75] Inventors: Zenichi Yoshida, 281, Ginza-cho 4-chome, Fushimi-ku, Koyto-shi, Kyoto-fu; Susumu Kato, Sakai; Yashuhiro Amemiya, Hirakata, all of Japan

[73] Assignees: Chemical Company, Ltd. Asahi, Osaka; Zenichi Yoshida, Kyoto, both of Japan

[21] Appl. No.: 53,022

[22] Filed: May 22, 1987

[30] Foreign Application Priority Data

Aug. 4, 1986 [JP] Japan ................................ 61-183149
Nov. 18, 1986 [JP] Japan ................................ 61-274992
Mar. 30, 1987 [JP] Japan ................................ 62-78477

[51] Int. Cl.$^4$ ............................................. C07C 2/86
[52] U.S. Cl. ..................................... 585/357; 585/360; 585/375; 585/376; 585/467

[58] Field of Search ............... 585/357, 360, 375, 376, 585/467

[56] References Cited

U.S. PATENT DOCUMENTS

| | | | |
|---|---|---|---|
| 3,251,897 | 5/1966 | Wise .................................... | 585/375 |
| 3,255,267 | 6/1966 | Fritz et al. .......................... | 585/375 |
| 4,567,308 | 1/1986 | Yoshida et al. ..................... | 585/376 |

OTHER PUBLICATIONS

Otouma et al, "Bull. Chem. Soc. Japan", 42(2449), 1969.

*Primary Examiner*—Patrick P. Garvin
*Assistant Examiner*—George R. Fourson
*Attorney, Agent, or Firm*—Armstrong, Nikaido, Marmelstein & Kubovcik

[57] ABSTRACT

A process for producing an alkylcyclopentadiene derivative comprising the vapor-phase reaction of a cyclopentadiene derivative and an aliphatic lower alcohol in the presence of a basic crystalline aluminosilicate catalyst containing an alkali metal.

16 Claims, No Drawings

PROCESS FOR PRODUCING ALKYLCYCLOPENTADIENE DERIVATIVES

The invention relates to a process for producing alkylcyclopentadiene derivatives.

Cyclopentadienes and alkylated products thereof are important as an additive for synthetic rubbers, starting materials for resins or industrial chemicals.

The following methods are known as alkylation of a cylcopentadiene derivative with an alcohol.

Firstly, U.S. Pat. No. 3,255,267 discloses a preparation of alkylated derivatives of cyclopentadiene by a reaction of cyclopentadiene or an alkylcyclopentadiene with an alcohol in the presence of a strong basic catalyst such as potassium or sodium hydroxide or alkoxide. However, the reaction is carried out in a liquid-phase, for example, batchwise at an increased pressure with use of an autoclave, or continuously at a pressure of 4,000 psi. Further, attention should be drawn to the fact that, as disclosed in the patent, only a tarry product was obtained when alkylation of cyclopentadiene with methanol was attempted. Thus, the patent describes it is impossible to produce a methylated derivative of cyclopentadiene.

Hirsch and Bailey disclose a preparation of 1,2,3,4,5-pentabenzylcyclopentadiene by a reaction of cyclopentadiene dimer with benzyl alcohol and sodium benzyloxide under reflux condition (J. Org. Chem., Vol. 43, No. 21, pages 4090~4094, 1978). The reaction is also conducted in a liquid-phase and involves a removal of aqueous layer during reaction. Moreover, a gel of sodium benzoate deposits when the reaction mixture is allowed to cool. Thus, this process requires a cumbersome means to remove aqueous layer during reaction and has a problem in purification of a product and in recovery of the catalyst.

Further, the present inventors disclose, in U.S. Pat. No. 4,567,308 (based on Japanese unexamined patent publication No. 202828/1985, Japanese patent application Nos. 237272/1984 and 29927/1985), a vapor phase reaction of a cyclopentadiene derivative with an aliphatic lower alcohol in the presence of a catalyst containing oxides such as an alkaline earth metal oxide or alkali metal oxide. As shown in this patent, basic solid catalysts are effectively used for the vapor phase alkylation of a cyclopentadiene with an alcohol.

It is further disclosed in this patent that, when aromatic compound is alkylated with an alcohol in the nucleus by vapor-phase reaction with use of zeolite catalysts as an acid catalyst, a corresponding alkylated aromatic compound can be produced. This catalyst, however, when applied to the process for preparing alkylcyclopentadienes, cannot produce any alkylated derivative but forms a polymerized product, carbonized product on the catalyst and like products by side reactions.

Conventionally, zeolite catalysts are known as an acid catalyst. Particularly zeolites in which an alkali metal cation is replaced by other metal cation exhibit strong acidity. It is known, on the other hand, that a basic zeolite is obtained by replacing a cation with an alkali metal. For example, Yashima et al disclose an alkylation of toluene with methanol with use of zeolite X or Y in which cations are replaced by alkali metals in J. Catalysis Vol. 26, pages 303~312 (1972). In the above, they report toluene is alkylated in the side chain with use of zeolite replaced by Na, K, Rb or Cs to give styrene and ethylbenzene, whereas tolene is alkylated in the ring to produce xylene when zeolite replaced by Li is used. Further they mention the formation of styrene and ethylbenzene depends on the basicity of the catalyst and the formation of xylene depends on the catalyst acidity.

In Japanese unexamined patent publication No. 205334/1984, is disclosed an alkylation of toluene with methanol with use of faujasite type zeolite which is obtained by replacing sodium in the zeolite with potassium and thereafter with cesium. This method showed the zeolite has strong basicity and improved catalytic property when about 80 to 90% of sodium was replaced by potassium and cesium.

Many patents are known which recite the alkylation of aromatic compounds in the side chain whith use of zeolite X or Y replaced by alkali metals as typically exemplified in the above. However, none of alkylation is reported which comprises a reaction of a cyclopentadiene derivative with an aliphatic lower alcohol in vapor-phase by use of a crystalline aluminosilicate catalyst containing an alkali metal.

An object of the invention is to provide a process for preparing alkylcyclopentadiene derivatives which comprises a reaction of a cyclopentadiene derivative with an aliphatic lower alcohol in vapor-phase with use of a specific catalyst which has a higher activity than conventional catalyst and novel features as later shown.

The above and other objects will become apparent from the following description.

The present invention provides a process for producing an alkylcyclopentadiene derivative comprising the vapor-phase reaction of a cyclopentadiene derivative with an aliphatic lower alcohol in the presence of a crystalline aluminosilicate catalyst containing an alkali metal.

In the vapor-phase alkylation of a cyclopentadiene derivative with an aliphatic lower alcohol with use of the above specific catalyst, pentaalkylated product can firstly be obtained in a large amount and tetraalkylated products are also produced in particularly large amount. Thus the catalyst used in the invention is most suitable for producing highly alkylated cyclopentadiene derivatives. Further the present catalyst is economically useful because it makes possible to reduce an amount of alcohol consumed in the reaction.

Examples of useful cyclopentadienes in the invention are cyclopentadiene, monomethylcyclopentadiene, cyclopentadiene dimer, methylcyclopentadiene dimer and like dimers and alkylated derivative thereof with alkyl group of 1 to 10 carbon atoms.

Examples of aliphatic lower alcohols used in the invention are those having 1 to 4 carbon atoms. More specific examples are methanol, ethanol, propanol and butanol.

The first group of the catalysts used in the present invention is a zeolite having alkali metal cations, which are for example those prepared without a substantial change of the starting zeolite crystal structure. Zeolites have basically a three dimensional network structure composed of $SiO_4$ and $AlO_4$. The zeolites used in the present invention have an atomic ratio (Z) of Si to Al, namely $Z = Si/Al$, of usually 0.9 to 10, preferably 1 to 5 and more preferably 1 to 4. Each of zeolites have pores which influence greatly on the present reaction. For the present reaction, useful are zeolites having pore sizes of at least 5 Å, preferably 7 to 10 Å in diameter. Preferred examples are zeolites having faujasite structure and zeolite L. As faujasite type zeolites are known a natural one and synthetic ones known as X-type and Y-type and, both are usable as a catalyst.

In the present invention, the crystalline aluminosilicate containing an alkali metal can be prepared, without a substantial change of the starting zeolite crystal structure, by contacting a zeolite with an alkali metal compound selected from the group consisting of a halide, hydroxide, carbonate, nitrate and organic acid salt of an alkali metal. In the above, the resulting crystalline aluminosilicate can be used and after removing or without removing an anion derived from the alkali metal compound. When nitrate is used as the alkali metal compound, it is preferable to remove the anion (nitrate ion). Examples of useful halides, hydroxides, carbonates, nitrates and organic acid salts of alkali metals are LiCl, NaCl, KCl, RbCl, CsCl, LiOH, NaOH, KOH, RbOH, CsOH, $Na_2CO_3$, $K_2CO_3$, $Rb_2CO_3$, $Cs_2CO_3$, $LiNO_3$, $NaNO_3$, $KNO_3$, $RbNO_3$, $CsNO_3$, $CH_3COOLi$, $CH_3COONa$, $CH_3COOK$, $CH_3COORb$, $CH_3COOCs$, etc.

The above catalyst of the present invention can be prepared by a usual ion exchange technique and for example prepared by contacting a zeolite with a solution of an alkali metal cation having various concentrations to replace sodium, hydrogen or other cation by the alkali metal cation in the solution.

The ion exchange reaction can be conducted in a medium such as water and an organic medium including alcohol, ketone, amide or a polar organic solvent and a mixture thereof. Examples of organic media are methanol, ethanol, isopropanol, acetone, dimethyl formamide, tetrahydrofuran, etc.

In case of preparing zeolite having at least two kinds of cations, it is advantageous to exchange a cation first with an alkali metal of lower basicity and then with that of higher basicity in order, from the viewpoint of catalyst property and economy. It is further possible to first exchange a part of cations with hydrogen ions and then to introduced the desired alkali metal cations. When zeolites are baked at several hundred degrees centrigrade, sodium ions in a narrow area are known to be replaced by cations in a wide area. After this baking, zeolites having a low sodium concentration can be obtained by replacing the sodium ions by the desired ions.

Examples of crystalline aluminosilicates having removed an anion therefrom are K.Na.X (this means zeolite X containing potassium and sodium ions, similar abbreviation is used hereinafter), Na.X, Rb.Na.X, Cs.Na.X, Cs.K.Na.X, Cs.Li.Na.X, K.Na.Y, Cs.K.Na.Y, K.Na.L, etc.

Among the above zeolites, those having a high content of Li cation or Na cation, for example, Li.Na.X and Li.Na.Y have strong acidity and especially zeolites having a high Li content are not preferable as a catalyst of the invention. However, these zeolites having strong acidity can be used as the present catalyst, after ion-exchanged by a cation having strong basicity such as K, Rb or Cs cation, or after brought into contact with alkali metal hydroxide, alkali metal carbonate or alkali metal salt of an organic acid.

These zeolites are usable as powder or a shaped product prepared with use of molding additive. Further, a shaped product obtained without containing molding additive such as Baylith of Bayer AG is also used as the present catalyst.

Although cation exchange of zeolites is generally conducted with use of a solution of neutral salts, alkali metal hydroxide is also usable as a cation source. The present catalyst is peferably used as it remains crystal structure of zeolite to be exchanged by alkali metal cation as highly as possible. When zeolite is contacted with a solution of alkali metal hydroxide of high concentration, crystal structure therof may be partially or almost destroyed. Accordingly, in case of using alkali metal hydroxide, mild conditions have to be employed in order to prevent destruction of zeolite structure. However, those are usable as the catalyst in which zeolite structure is partially destroyed or changed to another crystal structure. These ion exchanges are usually conducted at room temperatures but are increased in exchange velocity by heating.

The second group of the catalyst used in the present invention is a crystalline aluminosilicate which is prepared with a substantial change of the starting zeolite crystal structure. The substantial change means destruction of a part or whole of the crystal structure, and includes formation of crystalline aluminosilicates having different crystal structures from the starting zeolite. For example, zeolite A has pore sizes of 3 to 5 Å and the reaction hardly occurs in these pores. However, zeolite A is contacted with an alkali metal hydroxide, etc. to destroy crystal structure thereof and then used as the present catalyst. As an example of changing crystal structure of zeolite A or X by the contact with sodium hydroxide, Takahashi et al disclose, in Nippon Kagaku Zasshi (Journal of the Chemical Society of Japan, Pure Chemistry Section), vol. 89, pages 373~377 (1968), the preparation of faujasite type zeolite from halloysite and aqueous solution of sodium hydroxide. In the above, it is further disclosed that faujasite type zeolite finally changes into hydroxysodalite by the contact with sodium hydroxide.

Hino et al. disclose, in Nippon Kagaku Kaishi (Journal of the Chemical Society of Japan, Chemistry and Industrial Chemistry), pages 1847~1851 (1975), the preparation of zeolite A from mixtures of ethyl orthosilicate, sodium aluminate and aqueous solution of sodium hydroxide. It is further described that zeolite A changes into noselite which is known as feldspathoid when heated with maintaining $SiO_2/Al_2O_3$ molar ratio=1, and varing $Na_2O/SiO_2$ molar ratio in the range of 2 to 6. Sodalite and noselite are investigated in detail by R. M. Barrer et al. They disclose in J. Chem. Soc., vol. 1952, pages 1561~1571, the preparation of many feldspathoids and zeolites by hydrothermal reaction of aluminosilicate gel. For example, basic sodalite, basic noselite, etc. are prepared from the gel composed of $Al_2O_3$ and $SiO_2$ (molar ratio 1:2) in the presence of excess of sodium hydroxide.

Further, they report the preparation of feldspathoids and zeolite from kaolin and aqueous solutions of various alkali metal hydroxides in J. Chem. Soc. (A) vol. 1968, pages 2475~2485. A part of crystalline aluminosilicate used in the present invention prepared with a substantial change of crystal structure includes hydroxysodalite and like zeolite and feldspathoids.

In the present invention, the above second group of the catalysts is prepared, for example, by contacting zeolite with hydroxide, carbonate, organic acid salt of alkali metal or a mixture therof. Example of useful hydroxides, carbonates or organic acid salts of alkali metals are LiOH, NaOH, KOH, RbOH, CsOH, $Li_2CO_3$, $Na_2CO_3$, $K_2CO_3$, $Rb_2CO_3$, $Cs_2CO_3$, $CH_3COOLi$, $CH_3COONa$, $CH_3COOK$, $CH_3COORb$ and $CH_3COOCs$.

Further, the second group of the present catalyst includes a crystalline aluminosilicate prepared by contacting zeolite with a mixture of alkali metal hydroxide and alkali metal salt. Alkali metal salts, which are used in mixture with alkali metal hydroxide, include halides, sulfides and oxyacid salts of alkali metals. Examples of oxyacid salts are sulfate, phosphate, metasilicate, tungstate, aluminate, stannate, molybdate, etc. Examples of useful alkali metal salts are NaCl, $Na_2S$, $Na_2SO_4$, $Na_3PO_4$, $Na_2SiO_3$, $Na_2WO_4$, $NaAlO_2$, $Na_2SnO_3$, $NaMoO_4$, etc.

In the present invention, various zeolites are usable as the starting zeolite but particularly preferable are zeolites A, X, Y and L. These zeolites contain various kinds of cations. These cations may be those having 1 to 3 valencies, preferably those having 1 to 2 valencies. Examples thereof are metal ion-type zeolites containing alkali metal, alkaline earth metal or a mixture of these metals, zeolites A, X, Y and L containing hydrogen ion, ammonium ion or organic ammonium ion. More specific examples are K.Na.A, Na.A, Ca.Na.A, Na.X, K.Na.X, Li.Na.X, Rb.Na.X, Cs.Na.X, Cs.K.Na.X, Ca.Na.X, Ba.Na.X, Li.Na.Y, K.Na.Y, Rb.Na.Y, Cs.K.Na.Y, Li.K.Na.L, K.Na.L, Rb.K.Na.L, Cs.K.Na.L, etc.

The above zeolites A, X, Y and L are usable as powder or a shaped product prepared with use of molding additive. Further, a shaped product obtained without containing molding additive such as Baylith of Bayer AG is directly treated with alkali metal hydroxide, etc. to prepare the present catalyst.

In the preparation of the present catalyst with use of, for example, zeolite A, X, Y or L, each containing sodium ion as a cation, 0.05 to 4 moles, preferably 0.25 to 1 mole of hydroxide, carbonate, organic acid salt of alkali metal or a mixture thereof (hereinafter referred to as "alkali metal hydroxide, etc.") and 50 ml to 2 l, preferably 100 to 300 ml of water are used per 100 g of zeolite as specified by zeolite A being $Na_2O.Al_2O_3.2SiO_2.4.5H_2O$, zeolite X being $Na_2O.Al_2O_3.2.5SiO_2.6H_2O$, zeolite Y being $Na_2O.Al_2O_3.4.9SiO_2.8.9H_2O$ and zeolite L being $K_2O.Al_2O_3.6SiO_2.4.9H_2O$. An alkali metal salt, which is used in mixture with alkali metal hydroxide, is used in an amount of 0.01 to 2 moles, preferably 0.1 to 0.5 mole per 0.05 to 4 moles, preferably 0.25 to 1 mole of alkali metal hydroxie. Although alkali metal hydroxide, etc. and water are usable in an amount out of the above range, it becomes greatly difficult to substantially change crystal structure and requires longer time for the change, hence disadvantageous economically. The change of crystal structure is conducted in room temperature to 800° C., preferably at 50° to 500° C. With high temperature above 800° C., the change proceeds with difficulty and uneconomically. Further the change is conducted at an atmospheric pressure or inreased pressure.

In the above change of crystal structure, directly to zeolite can be added an aqueous solution of alkali metal hydroxide, etc., or a mixture of alkali metal hydroxide and alkali metal salt. Alternatively, to a slurry of zeolite in water can be added an solution of the above alkali metal hydroxide, etc., and the mixture is treated for a prescribed time at room temperature or with heating. The product is filtered and dried without washing or after washing with a small amount of water. In the case of using an appropriate amount of alkali metal hydroxide, etc., zeolite can be mixed with alkali metal hydroxide, etc., and the mixture is reacted for a prescribed time and dried without filtration to remove water to obtain the desired product. The resulting changed products can be made into the desired shape and used as the present catalyst. This is the same when a mixture of alkali metal hydroxide and alkali metal salt is used.

It is well known that zeolite is generally obtained with use of a mixture, as the starting materials, of ethyl orthosilicate, silica gel, silica sol, sodium silicate, sodium metasilicate or like silica source, aluminum alkoxide, sodium aluminate, aluminum hydroxide sol, aluminum chloride or like aluminum source, and alkali metal hydroxide, alkali metal alkoxide or like alkali source.

Further, zeolite can be obtained with use of natural minerals as the starting materials. For example, it is disclosed in [Zeolites, Foundation and Application] edited by Hara and Takahashi, pages 48~50 (1981), Kodan-sha Scientific Publication, the use of clay minerals, rocks, natural zeolites and like silicate minerals as the starting materials.

The present catalysts are not only those obtained by change of crystal structure of zeolite A, X, Y or L, but also those obtained by preparing crystalline aluminosilicates from the starting materials for zeolite A, X, Y or L without isolating the formed zeolite A, X, Y or L. The above catalyst preferably contains no impurity but may contain a small amount thereof.

The present catalysts are preferably calcined to enhance their activity at a temperature of 200° to 1000° C., more preferably at 400° to 800° C. in an atmosphere of air, nitrogen, helium, argon or like inert gas under normal, increased or reduced pressure.

Carbonized substances may adhere to the catalyst after a prolonged use thereof. In this case, it is possible to regenerate the catalyst by calcination at a temperature of 300° to 900° C., preferably at 400° to 800° C. in an atmosphere of air or oxygen-containing gas.

In the invention, each of a cyclopentadiene derivative and an aliphatic lower alcohol can be introduced to the catalyst layer in the form of a liquid, gas or a mixture of a liquid and gas. Further, it is preferable to supply nitrogen, helium, argon or like inert gas, water vapor, a small amount of air or oxygen, to enhance the activity of the catalyst and extend a catalyst life. The reaction zone is maintained usually at a temperature of 200° to 700° C., preferably at 400° to 550° C. With too low in the reaction temperature, the reaction velocity becomes slow, and with too high in the reaction temperature, side reactions occur, both not preferable in economical points. The reaction is conducted preferably at an atmospheric pressure but can be carried out at an reduced or increased pressure. The reaction may proceed in batchwise or continuous process and is conducted in various processes which are adoptable to vapor-phase reaction. Selectivity of the resulting alkylcyclopentadiene derivatives, for example, proportions of monoalkylated, dialkylated, trialkylated, tetraalkylated, pentaalkylated derivative and the like can be varied depending on the reaction conditions such as kinds and methods of preparation of the catalyst, molar ratios of the starting cyclopentadiene derivative and aliphatic lower alcohols, reaction temperature, feed velocity of the starting materials to the catalyst layer or the like.

The invention will be described with reference to the following Reference Example and Examples.

REFERENCE EXAMPLE 1

In 1200 ml of 0.5N—NaCl aq. solution was immersed 400 g of Baylith WE894 [4 to 13 mesh, spherical zeolite X, a product of Bayer AG]. After several hours, the supernatant liquid was removed by decantation and the residue was immersed again in NaCl aq. solution. After the above procedures were repeated three times, the residue was washed with pure water to remove the anion and then dried at 110° C. The resulting ion-exchanged zeolite was preserved in a desiccator having incorporated a saturated aqueous solution of ammonium chloride therein.

In 600 ml of 1N—KCl aq. solution was immersed Na.X (100 g) obtained by the above method. After reflux with heating for about 4 hours, the supernatant liquid was removed by decantation, and the residue was immersed again in KCl aq. solution and refluxed with heating. After these procedures were repeated 3 times, the residue was washed by the above-mentioned way and dried to obtain K.Na.X.

In the same manner as above, Cs.K.Na.X was prepared from K.Na.X (50 g) and 300 ml of 1N—CsCl aq. solution.

In the following examples, each of zeolites exchanged by alkali metal cation was prepared in the same manner as above. As zeolite Y was used ZCE-50 containing molding additive, 3 mm in diameter and about 4 mm in long, and ZCP-50, powder (both being products of Catalysts & Chemicals Ind. Co., Ltd.). Unless otherwise specified in the following, ZCP-50 was used as zeolite Y. As zeolite L was used TSZ-500 KOA (powder, a product of Toyo Soda Manuf. Co., Ltd.).

Ion-exchanged zeolites used in Examples 1 to 11 were checked for an amount of cation by flame photometry and the molar ratio was shown below.

| K.Na.X; | K/Na = 1.03 |
|---|---|
| Rb.Na.X; | Rb/Na = 0.774 |
| Cs.Na.X; | Cs/Na = 0.662 |
| Cs.K.Na.X; | Cs/Na = 1.32 |
| | K/Na = 0.895 |
| Cs.K.Na.Y; | Cs/Na = 6.78 |
| (ZCE-50) | K/Na = 5.40 |
| Cs.K.Na.Y; | Cs/Na = 5.45 |
| | K/Na = 3.74 |
| K.Na.Y; | K/Na = 6.23 |
| K.Na.L; | K/Na = 34.8 | uct was trapped by use of dry ice-acetone bath and was analysed by gas chromatography.

Conversions of methanol and cyclopentadiene dimer, and conversion based on cyclopentadiene derived from its dimer were 53.3%, 100% and 91.7% respectively. Selectivities of alkylcyclopentadienes were 5.79%, 5.20%, 5.12%, 21.6% and 16.5% respectively in monomethylated, dimethylated, trimethylated, tetramethylated and pentamethylated derivatives. Conversions of the starting materials and based on cyclopentadiene, and selectivity of alkylcyclopentadiene were given by the following equations.

$$\text{Conversion of the starting material (\%)} = 100 - \frac{\text{mole of recovered starting material}}{\text{mole of supplied starting material}} \times 100$$

$$\text{Conversion based on cyclopentadiene (\%)} = 100 - \frac{\text{mole of recovered cyclopentadiene}}{\text{mole of cyclopentadiene deemed to be supplied}} \times 100$$

$$\text{Selectivity(\%)} = \frac{\text{mole of produced alkylcyclopentadiene}}{\text{mole of converted cyclopentadiene}} \times 100$$

EXAMPLE 2

The reaction was conducted in the same manner as in Example 1 except that methylcyclopentadiene dimer was used in place of cyclopentadiene dimer and the starting materials were supplied over a period of 1.83 hours. Conversions of methanol and methylcyclopentadiene dimer, and conversion based on methylcyclopentadiene were 40.6%, 100% and 98.3% respectively. Selectivities of alkylcyclopentadienes were 2.87%, 5.40%, 16.4% and 23.9% respectively in dimethylated, trimethylated, tetramethylated and pentamethylated derivatives.

EXAMPLES 3 TO 8

The reactions were conducted in the same manner as in Example 1. The results were shown in Table 1.

TABLE 1

| Ex | Catalyst (50 g) | Molar ratio | temp (°C.) | W/F | Conversion (%) Methanol | A | B | Selectivity (%) C | D | E | F |
|---|---|---|---|---|---|---|---|---|---|---|---|
| 3 | Na.X | 0.025/0.5 | 400 | 163 | 71.4 | 100 | 97.0 | 2.78 | 0.815 | 0.221 | 0.847 |
| 4 | K.Na.X | 0.025/0.5 | 400 | 163 | 85.6 | 100 | 88.4 | 6.43 | 1.56 | 0.613 | 0.485 |
| 5 | Rb.Na.X | 0.025/0.5 | 350 | 163 | 12.5 | 100 | 90.3 | 2.85 | 0.723 | 0.196 | 0.166 |
| 6 | Cs.Na.X | 0.025/0.5 | 400 | 163 | 78.6 | 100 | 97.2 | 3.45 | 2.47 | 2.17 | 1.83 |
| 7 | Cs.K.Na.X | 0.025/0.5 | 300 | 476 | 21.9 | 100 | 87.6 | 5.10 | 1.16 | 0.438 | 0.766 |
| 8 | Cs.K.Na.Y(ZCE-50) | 0.025/0.5 | 350 | 163 | 19.4 | 100 | 86.5 | 2.49 | 0.669 | 0.331 | 0.195 |

EXAMPLE 1

The reaction was conducted with use of a usual reaction apparatus of a fixed-bed flow method. The reaction tube is made of quartz glass and is one meter in length and 30 mm in inner diameter. The reaction tube was packed with 50 g of the calcined catalyst (Cs.K.Na.X) and the catalyst was further calcined at 450° C. for 3 hours while introducing nitrogen gas at a velocity of 90 ml/min. Then, the reaction zone was heated to 400° C. and thereto were introduced 0.025 mole of cyclopentadiene dimer and 0.5 mole of methanol over a period of 1.72 hours with use of microfeeder. The reaction prod- In the Table, Molar ratio is a value of (mole of used cyclopentadiene dimer derivative)/(mole of used alcohol).

W/F is a value of (catalyst amount, g)/(feed velocity of starting material, mole/hr).

A indicates methylcyclopentadiene dimer, B methylcyclopentadiene, C, D, E and F dimethylated, trimethylated, tetramethylated and pentamethylated derivatives of cyclopentadiene respectively.

EXAMPLES 9 TO 11

The reactions of methylcyclopentadiene dimer and methanol were conducted with use of a pulse reaction system and catalysts prepared in the same manner as in Reference Example 1. Prior to the reaction, distribution or amounts of products were confirmed to resemble to those in the flow process.

The reaction tube was made of quartz glass and was 110 mm in long and 6 mm in inner diameter. The reaction tube was packed with 0.15 g of the calcined catalyst having a particle size of 16 to 20 mesh and the catalyst was further calcined at 500° C. for 30 minutes while introducing nitrogen gas at a velocity of 40 ml/min. Thereto were introduced the starting materials at 500° C. by use of microsyringe. As one pulse was used 2 μl of a mixture of 0.05 mole of a cyclopentadiene dimer derivative, 1.0 mole of alcohol and 0.5 g of toluene as an internal standard used for quantitative analysis. The products were directly introduced to a connected gas chromatography and analysed. The results were given in Table 2, indicating the analysed value of the fifth pulse.

TABLE 2

| Ex | Catalyst | Conversion (%) Methanol | A | B | Selectivity (%) C | D | E | F |
|---|---|---|---|---|---|---|---|---|
| 9 | K.Na.Y | 28.0 | 100 | 89.5 | 6.67 | 2.45 | 0.402 | 0.400 |
| 10 | Cs.K.Na.Y | 29.8 | 100 | 96.5 | 8.12 | 9.05 | 4.36 | 1.29 |
| 11 | K.Na.L | 37.4 | 100 | 99.4 | 2.15 | 6.09 | 23.6 | 8.07 |

EXAMPLE 12

As zeolite X was used Zeolum F9 (powder, a product of Toyo Soda Manuf. Co., Ltd.). Hereinafter, unless otherwise specified, used were powdery products of Toyo Soda Manuuf. Co., Ltd. as zeolite X or A.

To 200 g of Zeolum F9 was added 400 ml of water with stirring to obtain a slurry. Thereto was added 400 ml of sodium hydroxide of 12.5 moles/l concentration and the mixture was stirred at 90° C. for one hour. The resulting slurry was filtered and dried to a solid at 110° C. The solid was pulverized to particles 5 to 9 mesh in size and calcined at 500° C. for 3 hours under nitrogen stream to prepare a catalyst for use to the reaction.

The reaction was conducted with use of the same apparatus as in Example 1. The reaction tube was packed with 100 g of the calcine catalyst and the catalyst was further calcined at 500° C. for 3 hours while introducing nitrogen gas at a velocity of 90 ml/min. Then, the reaction zone was heated to 450° C. and thereto were introduced 0.025 mole of cyclopentadiene dimer and 0.5 mole of methanol over a period of 1.36 hours with use of microfeeder. The reaction product was trapped by use of dry ice-acetone bath and was analysed by gas chromatography.

Conversions of methanol and cyclopentadiene dimer, and conversion based on cyclopentadiene derived from its dimer were 44.9%, 100% and 87.5% respectively. Selectivities of alkylcyclopentadienes were 25.1%, 13.7%, 2.32%, 1.05% and 2.35% respectively in monomethylated, dimethylated, trimethylated, tetramethylated and pentamethylated derivatives.

EXAMPLE 13

To zeolite X powder (150 g) was added 200 ml of an aqueous solution of sodium hydroxide having a concentration of 2.81 moles/l with thorough stirring. The mixture was dried to solid at 90° C. The solid was pulverized to particles 5 to 9 mesh in size and calcined at 500° C. for 3 hours under nitrogen stream to prepare a catalyst for use to the reaction.

The reaction was conducted in the same manner as in Example 12 except that methylcyclopentadiene dimer was used in place of cyclopentadiene dimer and the starting materials were introduced over a period of 2.22 hours. Conversions of methanol and methylcyclopentadiene dimer, and conversion based on methylcyclopentadiene were 92.6%, 100% and 97.7% respectively. Selectivities of alkylcyclopentadienes were 6.73%, 7.76%, 14.8% and 47.6% respectively in dimethylated, trimethylated, tetramethylated and pentamethylated derivatives.

EXAMPLES 14 TO 19

The reactions were conducted in the same manner as in Example 13. Table 3 shows the results.

TABLE 3

| Ex. | Catalyst (g) Zeolite | Alkali metal hydroxide | molar ratio | temp (°C.) | W/F | Conversion (%) Methanol | A | B | Selectivity (%) C | D | E | F |
|---|---|---|---|---|---|---|---|---|---|---|---|---|
| 14 | Na.X (100) | LiOH.H$_2$O (20.0) | 0.05/1.0 | 450 | 167 | 35.9 | 100 | 77.9 | 30.0 | 5.17 | 0.950 | 1.27 |
| 15 | Na.X (100) | KOH (20.0) | 0.05/1.0 | 450 | 158 | 44.7 | 100 | 84.7 | 29.5 | 9.31 | 1.30 | 1.46 |
| 16 | Na.X (100) | RbOH (50.0) | 0.05/1.0 | 450 | 155 | 55.9 | 100 | 87.1 | 22.6 | 10.3 | 1.66 | 0.270 |
| 17 | Na.X (100) | CsOH (100) | 0.05/1.0 | 500 | 135 | 57.8 | 100 | 93.8 | 21.2 | 22.4 | 6.22 | 1.12 |
| 18 | K.Na.A (150) | NaOH (20.0) | 0.025/0.5 | 450 | 255 | 35.6 | 100 | 97.1 | 19.5 | 20.4 | 4.28 | 0.383 |
| 19 | Na.Y (100) | NaOH (20.0) | 0.025/0.5 | 450 | 223 | 69.6 | 100 | 83.3 | 13.2 | 4.63 | 25.5 | 17.9 |

EXAMPLE 20

To 50 g of spherical zeolite X [Baylith WE894 (4 to 18 mesh), a product of Bayer AG] was added 400 ml of an aqueous solution of potassium hydroxide of 4.46 moles/l concentration with thorough stirring. The mixture was allowed to stand at room temperature for 3 days. The mixture was filtered, dried at 110° C. without washing and calcined at 500° C. for 3 hours under nitrogen stream to prepare a catalyst.

The reaction was conducted in the same manner as in Example 12 except that, per 50 g of the catalyst, 1.0 mole of methanol and 0.05 mole of methylcyclopentadiene dimer were introduced to the reaction zone at 450° C. over a period of 1.9 hours. Conversions of methanol and methylcyclopentadiene dimer, and conversion based on methylcyclopentadiene were 66.3%, 100% and 84.7% respectively. Selectivities of alkylcyclopentadienes were 12.8%, 7.31%, 2.59% and 0.746% respectively in dimethylated, trimethylated, tetramethylated and pentamethylated derivatives.

EXAMPLE 21

In the same manner as in Example 20, a catalyst was prepared with use of spherical zeolite X containing a binder [Zeolum F9 (12 to 20 mesh), a product of Toyo Soda Manuf. Co., Ltd.]. The reaction was conducted in the same manner as in Example 20 except that 0.5 mole of methanol and 0.05 mole of methylcyclopentadiene dimer were introduced to the reaction zone over a period of one hour. Conversions of methanol and methylcyclopentadiene dimer, and conversion based on methylcyclopentadiene were 43.7%, 100% and 76.6% respectively. Selectivities of alkylcyclopentadienes were 23.9%, 12.1%, 3.03% and 0.732% respectively in dimethylated, trimethylated, tetramethylated and pentamethylated derivatives.

EXAMPLES 22 TO 68

Catalysts were prepared in the same manner as in Example 13. The reaction was conducted with use of methylcyclopentadiene dimer and methanol by the pulse reaction system as disclosed in Example 9. The results were given in Table 4.

In Examples 12 to 68, molar ratios of cations in various ion-exchanged zeolites used were as follows.

| | |
|---|---|
| K.Na.A; | K/Na = 1.4, |
| Ca.Na.A; | Ca/Na = 3.8, |
| Li.Na.X; | Li/Na = 1.0, |
| K.Na.X; | K/Na = 2.0, |
| Rb.Na.X; | Rb/Na = 0.95, |
| Cs.Na.X; | Cs/Na = 0.85, |
| Cs.K.Na.X; | Cs/Na = 1.6, K/Na = 1.0, |
| Ca.Na.X; | Ca/Na = 0.48, |
| Ba.Na.X; | Ba/Na = 3.9 |
| K.Na.L; | K/Na = 34.8 |

TABLE 4

| Ex. | Catalyst (g) Zeolite | Alkali metal compound | Conversion (%) Methanol | A | B | Selectivity (%) C | D | E | F |
|---|---|---|---|---|---|---|---|---|---|
| 22 | Na.X (10.0) | NaOH (2.00) | 91.6 | 100 | 98.5 | 9.43 | 13.1 | 19.4 | 24.1 |
| 23 | K.Na.X (10.8) | KOH (2.81) | 86.1 | 100 | 96.3 | 18.7 | 30.1 | 12.0 | 2.48 |
| 24 | K.Na.X (10.8) | RbOH (5.12) | 56.6 | 100 | 95.3 | 20.4 | 27.7 | 11.6 | 3.03 |
| 25 | K.Na.X (10.8) | CsOH (7.50) | 90.6 | 100 | 98.7 | 5.34 | 9.06 | 6.53 | 2.92 |
| 26 | Cs.K.Na.X (200) | NaOH (0.200) | 83.1 | 100 | 96.7 | 15.1 | 23.4 | 11.4 | 3.12 |
| 27 | Li.Na.X (9.24) | LiOH.H$_2$O (4.20) | 96.8 | 100 | 96.4 | 19.3 | 30.9 | 10.6 | 1.71 |
| 28 | Rb.Na.X (13.0) | NaOH (2.00) | 87.6 | 100 | 92.5 | 19.3 | 28.6 | 13.7 | 3.30 |
| 29 | Ca.Na.X (20.0) | NaOH (10.0) | 93.9 | 100 | 92.8 | 25.2 | 21.4 | 5.03 | 1.25 |
| 30 | Ba.Na.X (3.00) | NaOH (1.50) | 85.4 | 100 | 89.8 | 28.6 | 18.6 | 5.01 | 0.866 |
| 31 | Na.A (10.0) | NaOH (5.00) | 85.3 | 100 | 77.1 | 23.9 | 7.69 | 1.97 | 0.519 |
| 32 | Ca.Na.A (10.0) | NaOH (2.00) | 57.8 | 100 | 76.7 | 37.0 | 6.58 | 2.32 | 3.06 |
| 33 | K.Na.A (1.00) —Na.X (9.00) | NaOH (2.00) | 27.5 | 100 | 66.9 | 39.6 | 5.43 | 0.556 | 0.408 |
| 34 | Na.Y (10.0) | LiOH (1.05) | 38.3 | 100 | 99.0 | 0.782 | 0.902 | 2.15 | 1.21 |
| 35 | Na.Y (20.0) | NaOH (2.00) | 71.5 | 100 | 99.0 | 0.427 | 1.39 | 12.3 | 5.74 |
| 36 | Na.Y (10.0) | KOH (1.40) | 59.1 | 100 | 99.5 | 0.882 | 3.56 | 28.6 | 15.7 |
| 37 | Na.Y (10.0) | RbOH (2.56) | 71.1 | 100 | 98.5 | 1.44 | 5.21 | 28.2 | 14.7 |
| 38 | Na.Y (10.0) | CsOH (3.75) | 89.9 | 100 | 99.8 | 0.355 | 3.30 | 29.1 | 16.1 |
| 39 | K.Na.L (10.0) | LiOH (2.10) | 60.8 | 100 | 87.8 | 11.8 | 14.3 | 35.1 | 17.0 |
| 40 | K.Na.L (10.0) | NaOH (0.500) | 19.4 | 100 | 53.9 | 40.5 | 8.97 | 3.29 | 0.615 |
| 41 | K.Na.L (10.0) | KOH (1.40) | 67.0 | 100 | 83.7 | 26.9 | 18.8 | 18.2 | 2.13 |
| 42 | K.Na.L (10.0) | RbOH (2.56) | 78.4 | 100 | 81.8 | 28.7 | 17.6 | 12.5 | 1.22 |
| 43 | K.Na.L (10.0) | CsOH (3.75) | 61.6 | 100 | 82.4 | 24.3 | 18.4 | 19.6 | 3.83 |
| 44 | Na.A (20.0) | Na$_2$CO$_3$ (2.00) | 41.3 | 100 | 25.2 | 14.2 | 0.707 | 2.21 | — |
| 45 | Na.X (20.0) | Na$_2$CO$_3$ (8.00) | 89.6 | 100 | 99.7 | 0.881 | 2.95 | 22.1 | 8.73 |
| 46 | Na.Y (20.0) | Na$_2$CO$_3$ (2.00) | 23.7 | 100 | 99.4 | 0.631 | 3.63 | 26.1 | 18.2 |
| 47 | K.Na.L (20.0) | Na$_2$CO$_3$ (2.00) | 64.5 | 100 | 95.7 | 9.17 | 11.8 | 32.4 | 10.8 |
| 48 | Na.A | K$_2$CO$_3$ | 45.1 | 100 | 42.7 | 30.8 | 3.59 | 8.53 | 1.53 |

TABLE 4-continued

| | Catalyst (g) | | Conversion (%) | | | Selectivity (%) | | | |
|---|---|---|---|---|---|---|---|---|---|
| Ex. | Zeolite | Alkali metal compound | Methanol | A | B | C | D | E | F |
| | (20.0) | (10.4) | | | | | | | |
| 49 | Na.X (20.0) | $K_2CO_3$ (10.4) | 84.6 | 100 | 82.2 | 7.17 | 3.43 | 4.79 | 2.94 |
| 50 | Na.Y (10.0) | $K_2CO_3$ (1.31) | 53.4 | 100 | 99.3 | 0.679 | 4.54 | 23.1 | 9.67 |
| 51 | K.Na.L (20) | $K_2CO_3$ (10.4) | 48.7 | 100 | 77.0 | 26.1 | 19.4 | 19.2 | 2.95 |
| 52 | Na.A (20) | $CH_3COONa$ (10.3) | 53.1 | 100 | 40.5 | 16.4 | 1.22 | 7.19 | 1.15 |
| 53 | Na.X (20) | $CH_3COONa$ (10.3) | 74.4 | 100 | 50.3 | 12.2 | 2.13 | 4.47 | 1.69 |
| 54 | Na.Y (10) | $CH_3COONa$ (5.15) | 47.0 | 100 | 99.5 | — | 2.53 | 31.2 | 19.5 |
| 55 | K.Na.L (20) | $CH_3COONa$ (10.3) | 34.5 | 100 | 50.0 | 23.3 | 3.58 | 1.80 | — |
| 56 | Na.Y (10.0) | $Cs_2CO_3$ (6.15) | 80.8 | 100 | 94.2 | 5.65 | 7.60 | 24.7 | 9.62 |
| 57 | K.Na.L (10.0) | $Rb_2CO_3$ (4.36) | 75.8 | 100 | 91.9 | 20.7 | 21.6 | 23.0 | 3.16 |
| 58 | K.Na.L (10.0) | $Cs_2CO_3$ (6.15) | 62.4 | 100 | 90.8 | 19.7 | 19.4 | 22.3 | 4.14 |
| 59 | Na.X (5.00) | $Na_2SO_4$ (0.670) NaOH (0.500) | 67.1 | 100 | 100 | — | 6.26 | 50.1 | 30.7 |
| 60 | Na.X (5.00) | $Na_2CO_3$ (0.500) NaOH (0.500) | 86.0 | 100 | 100 | — | 6.16 | 45.9 | 23.7 |
| 61 | Na.X (5.00) | NaCl (0.280) NaOH (0.500) | 87.8 | 100 | 100 | 3.64 | 6.78 | 16.3 | 3.91 |
| 62 | Na.X (5.00) | $Na_3PO_4$ (0.800) NaOH (0.500) | 77.3 | 100 | 98.5 | 3.25 | 6.35 | 16.4 | 3.90 |
| 63 | Na.X (5.00) | $Na_3SiO_3.9H_2O$ (1.34) NaOH (0.500) | 79.7 | 100 | 100 | 3.34 | 4.81 | 8.27 | 1.69 |
| 64 | Na.X (5.00) | $Na_2WO_4.2H_2O$ (1.56) NaOH (0.500) | 84.5 | 100 | 100 | 4.21 | 7.97 | 21.1 | 5.97 |
| 65 | Na.X (5.00) | $NaAlO_2$ (0.387) NaOH (1.00) | 42.6 | 100 | 65.3 | 19.6 | 5.74 | 30.8 | 14.6 |
| 66 | Na.X (5.00) | $Na_2SnO_3.3H_2O$ (1.26) NaOH (0.500) | 88.3 | 100 | 97.5 | 7.30 | 10.2 | 20.5 | 6.34 |
| 67 | Na.X (5.00) | $Na_2MoO_4.2H_2O$ (1.14) NaOH (0.500) | 68.1 | 100 | 100 | 4.16 | 9.49 | 23.5 | 5.76 |
| 68 | Na.X (5.00) | $Na_2S$ (1.13) NaOH (0.500) | 54.7 | 100 | 97.8 | 5.20 | 6.24 | 13.3 | 3.68 |

We claim:

1. A process for producing alkylcyclopentadiene compounds comprising vapor-phase alkylation of a cyclopentadiene compound selected from the group consisting of cyclopentadiene, alkylcyclopentadiene, wherein the alkyl group contains 1 to 10 carbon atoms, and dimers thereof, with an aliphatic lower alcohol in the presence of a basic crystalline aluminosilicate catalyst selected from the group consisting of (a) zeolites, wherein all exchangeable cations are alkali metal cations, and (b) crystalline aluminosilicate wherein the crystal structure has been modified.

2. A process as defined in claim 1 wherein the crystalline aluminosilicate catalyst which is a zeolite wherein all exchangeable cations are alkali metal cations is obtained without a substantial change of the crystal structure by contacting a zeolite with an alkali metal compound selected from the group consisting of halides, hydroxides, carbonates, nitrates and organic acid salts of an alkali metal.

3. A process as defined in claim 2 wherein the resulting crystalline aluminosilicate is used after removing an anion derived from the alkali metal compound.

4. A process as defined in claim 2 wherein the resulting crystalline aluminosilicate is used without removing an anion derived from the alkali metal compound.

5. A process as defined in claim 1 wherein the crystalline aluminosilicate catalyst having a crystal structure which has been modified is prepared by contacting a zeolite with a sufficient concentration of an alkali metal compound selected from the group consisting of hydroxide, carbonate, organic acid salt of an alkali metal and mixtures thereof, to effect a change in crystal structure.

6. A process as defined in claim 1 wherein the crystalline aluminosilicate catalyst having a crystal structure which has been modified is prepared by contacting a zeolite with a sufficient concentration of a mixture of an alkali metal hydroxide and an alkali metal salt selected from the group consisting of halide, sulfide, and oxyacid salt of an alkali metal, to effect a change in crystal structure.

7. A process as defined in claim 6 wherein the oxyacid salt of an alkali metal is sulfate, phosphate, metasilicate, tungstate, aluminate, stannate or molybdate.

8. A process as defined in claim 1 wherein the crystalline aluminosilicate has a Si/Al atomic ratio of 0.9 to 10.

9. A process as defined in claim 8 wherein the crystalline aluminosilicate has a Si/Al atomic ratio of 1 to 5.

10. A process as defined in claim 9 wherein the crystalline aluminosilicate is zeolite A, X, Y or L.

11. A process as defined in claim 1 wherein the cyclopentadiene compound which is alkylated is cyclopentadiene, cyclopentadiene dimer or alkylated derivative thereof with alkyl group of 1 to 10 carbon atoms.

12. A process as defined in claim 11 wherein the cyclopentadiene compound which is alkylated is cyclopentadiene, monomethylcyclopentadiene, cyclopentadiene dimer or methylcyclopentadiene dimer.

13. A process as defined in claim 1 wherein the aliphatic lower alcohol has 1 to 4 carbon atoms.

14. A process as defined in claim 13 wherein the aliphatic lower alcohol is methanol.

15. A process as defined in claim 1 wherein the alkylation is conducted at a temperature of about 200° to 700° C.

16. A process as defined in claim 15 wherein the alkylation is conducted at a temperature of about 300° to 500° C.

* * * * *

UNITED STATES PATENT AND TRADEMARK OFFICE
CERTIFICATE OF CORRECTION

PATENT NO. : 4,814,532

DATED : March 21, 1989

INVENTOR(S) : YOSHIDA et al

It is certified that error appears in the above-identified patent and that said Letters Patent is hereby corrected as shown below:

On the cover page, Item [73], "Chemical Company, Ltd. Asahi," should read --Asahi Chemical Company, Ltd.--.

Signed and Sealed this

Fourteenth Day of November, 1989

Attest:

JEFFREY M. SAMUELS

*Attesting Officer*  *Acting Commissioner of Patents and Trademarks*